(12) United States Patent
McGall et al.

(10) Patent No.: US 7,452,673 B2
(45) Date of Patent: Nov. 18, 2008

(54) PHOTOACID GENERATORS FOR THE SYNTHESIS OF OLIGO-DNA IN A POLYMER MATRIX

(75) Inventors: Glenn H. McGall, Palo Alto, CA (US); Andrea Cupoletti, Livermore, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 11/623,692

(22) Filed: Jan. 16, 2007

(65) Prior Publication Data

US 2007/0265366 A1 Nov. 15, 2007

Related U.S. Application Data

(60) Provisional application No. 60/760,324, filed on Jan. 18, 2006.

(51) Int. Cl.
| | |
|---|---|
| *C12Q 1/68* | (2006.01) |
| *C07C 315/00* | (2006.01) |
| *C07C 317/00* | (2006.01) |
| *C07C 205/00* | (2006.01) |
| *C07C 207/00* | (2006.01) |
| *C08F 2/46* | (2006.01) |
| *C07H 21/00* | (2006.01) |
| *C07H 21/02* | (2006.01) |

(52) U.S. Cl. .......... 435/6; 522/31; 522/59; 522/65; 536/23.1; 536/25.3; 568/29; 568/34; 568/30; 568/306; 568/325; 430/270.1

(58) Field of Classification Search .......... 568/29, 568/34, 30, 306, 325; 522/31; 435/6
See application file for complete search history.

(56) References Cited

U.S. PATENT DOCUMENTS 6,159,665 A * 12/2000 Chin et al. .......... 430/325
2004/0110133 A1 * 6/2004 Xu et al. .......... 435/6

FOREIGN PATENT DOCUMENTS

WO   WO 2006117556 A2 * 11/2006

* cited by examiner

*Primary Examiner*—Marc S. Zimmer
*Assistant Examiner*—Jessica Treidl
(74) *Attorney, Agent, or Firm*—Lisa T. Kajisa

(57) ABSTRACT

Compounds represented by the following structural formulas can be used as photoacid generators:

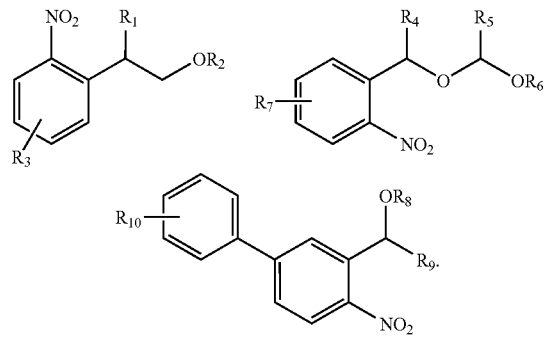

Such compounds are useful, for example, in fabricating arrays of polymers.

7 Claims, No Drawings

PHOTOACID GENERATORS FOR THE SYNTHESIS OF OLIGO-DNA IN A POLYMER MATRIX

BACKGROUND OF THE INVENTION

Methods of synthesizing polymer sequences such as nucleotide and peptide sequences are known. Synthesis of individual oligonucleotides is described in Oligonucleotide Synthesis: A Practical Approach, Gait, ed., IRL Press, Oxford (1984), incorporated herein by reference in its entirety for all purposes. Similarly, the "Merrifield" solid phase peptide synthesis has been in common use for many years and is discussed in Merrifield, *J. Am. Chem. Soc.* (1963) 85:2149-2154, incorporated herein by reference for all purposes.

The in situ fabrication of a plurality of polymers or "catamers," including peptides and oligonucleotides, on a single solid support (a plurality of pins attached to a support, each pin having a unique polymer) to subsequently be used for analytical purposes was described in WO86/06487, published Nov. 6, 1986, entitled "Method for determining mimotopes," by Hendrik M. Geysen, incorporated herein by reference for all purposes.

The combination of solid phase synthetic chemistry and photolithographic technology from the semiconductor industry allowed for the first time for the fabrication of high density arrays of polymers. See Fodor, S. P. A., Read, L. J., Pirrung, M. C., Stryer, L., Lu, A. T. and Solas, D., Light-Directed, Spatially Addressable Parallel Chemical Synthesis, (1991) *Science* 251, 767-773, incorporated herein by reference for all purposes.

These techniques disclosed in Fodor et al. provide for total independent access to sites on the substrate at each synthetic step, allowing for massive parallel synthesis of the desired polymer (e.g., peptide, oligonucleotide) on the array. In turn, combinatorial masking strategies allow for the fabrication of a large number of chemical entities in a relatively small number of steps. In addition, light-directed synthesis allows for a high degree of miniaturization because the density of synthesis sites is bounded only by physical limitations on spatial addressability, here the diffraction of light.

These photolithograph techniques have been employed commercially to produce high density oligonucleotide arrays which may be used, for example, to simultaneously monitor the expression of the entire set of human genes or to finely map the genome of a human subject. This technology has in turn led to diagnostic applications of the high density arrays for human disease. See www.affymetrix.com.

SUMMARY OF THE INVENTION

The present invention provides compounds represented by Structural Formula (I):

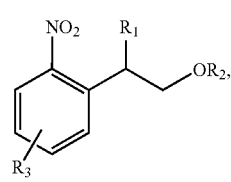

or a salt thereof, wherein:

$R_1$ is —H, —COOR, a substituted alkyl group, or an alkenyl or aryl group;

$R_2$ is a sulfonate, substituted acetate or benzoate group;

$R_3$ is —NRR', —COOR, an alkyl or alkenyl group or a substituted alkoxy or aryl group; and R and R' are independently —H or an alkyl, alkenyl or aryl group.

The invention also provides compounds represented by Structural Formula (II):

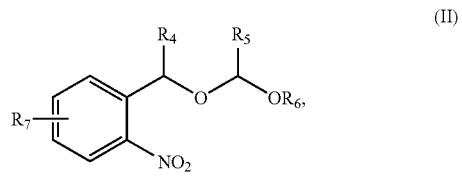

or a salt thereof, wherein:

$R_4$ and $R_5$ are independently —H, —COOR, a substituted alkyl group or an alkenyl or aryl group;

$R_6$ is a sulfonate, substituted acetate or benzoate group;

$R_7$ is —NRR', —COOR, an alkyl or alkenyl group or a substituted alkoxy or aryl group; and R and R' are independently —H or an alkyl, alkenyl or aryl group.

The invention additionally provides compounds represented by Structural Formula (III):

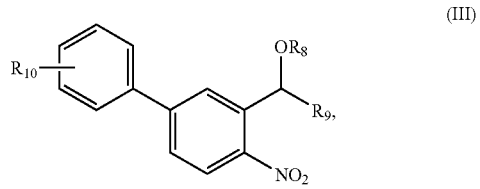

or a salt thereof, wherein:

$R_8$ is a sulfonate, substituted acetate or benzoate group;

$R_9$ is —H, —COOR, a substituted alkyl group or an alkenyl or aryl group;

$R_{10}$ is —NRR', —COOR, an alkyl or alkenyl group or a substituted alkoxy or aryl group; and R and R' are independently —H or an alkyl, alkenyl or aryl group.

In one aspect, the present invention discloses methods of generating acid by exposing a compound represented by one of Structural Formulae (I)-(III) to light of an appropriate wavelength.

In another aspect, the present invention discloses methods for fabricating arrays of polymers. One disclosed method includes the steps of: providing a solid substrate comprising a reactive group protected by an acid labile protective group; coating said solid substrate with a film, said film comprising a photoacid generator represented by Structural Formula (I), (II) or (III) and optionally an acid scavenger; activating said photo acid generator in selected regions of said substrate by selective application of light having a predetermined wavelength to provide an acid; exposing said reactive group having said protective group to said acid in the presence of said scavenger, when present, such that said protective group is removed to provide an exposed reactive group; reacting said exposed reactive group with a monomer, wherein the monomer is coupled to said exposed reactive group; and repeating the steps of coating, activating, exposing and reacting to produce the array of polymers.

In one aspect of the invention, the monomers are nucleotides and the polymer is an oligonucleotide. In another aspect of the invention, the monomers are amino acids and the polymer is a polypeptide.

Another method of the invention includes the steps of: providing a substrate comprising a hydroxyl group protected by an acid labile protective group; coating said substrate with a film, said film comprising a photo acid generator represented by one of Structural Formulae (I)-(III) and optionally an acid scavenger; activating said photo acid generator in selected regions of said substrate by selective application of light having a predetermined wavelength to provide an acid; exposing said hydroxyl group protected by said protective group to said acid in the presence of said scavenger, when present, such that said protective group is removed to produce a deprotected hydroxyl group; reacting said deprotected hydroxyl group with a nucleotide monomer, wherein the nucleotide monomer is coupled to said deprotected hydroxyl group; and repeating the steps of coating, activating, exposing and reacting to produce the array of oligonucleotides.

In an aspect of the invention, the method also includes the steps of: stripping the film from the substrate with an appropriate solvent after removal of the protective group to provide a partially completed substrate comprising an exposed reactive hydroxyl group; reacting said hydroxyl group with a deoxynucleotide with a reactive group at its 5' or 3' hydroxyl group and an acid labile protective group at the other 5' or 3' hydroxyl group; and repeating the steps of coating, activating, exposing, stripping, and reacting to provide the array of oligonucleotides. The above methods can also be applied to fabricate arrays of other polymers such as carbohydrates and nucleic acid peptides.

DETAILED DESCRIPTION OF THE INVENTION

Definitions

The following definitions are applicable to the terms set forth below unless otherwise indicated. Halogen or "halo" is fluoro, chloro, bromo, or iodo. Alkyl, alkoxy, aralkyl, alkylaryl, and the like denote both straight and branched groups; but reference to an individual radical such as "propyl" embraces only the straight chain alkyl group, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

"Alkyl" refers to a straight chain, branched or cyclic saturated chemical group containing only carbon and hydrogen. Alkyl groups include, without limitation, ethyl, propyl, butyl, pentyl, cyclopentyl and 2-methylbutyl. Alkyl groups are unsubstituted or substituted with 1 or more substituents (e.g., halogen, alkoxy, amino).

"Alkenyl" refers to a straight chain, branched or cyclic chemical group containing only carbon and hydrogen and having at least one double bond. Alkylene groups include, without limitation, ethenyl, propenyl, butenyl, pentenyl, and 2-methylbutenyl. Alkenyl groups are unsubstituted or substituted with 1 or more substituents (e.g., halogen, alkoxy, amino).

"Alkynyl" refers to a straight chain, branched or cyclic chemical group containing only carbon and hydrogen and having at least one triple bond. Alkynyl groups include, without limitation, ethylyne, propylene, butylyne, pentylyne and hexylyne. Alkynyl groups are unsubstituted or substituted with 1 or more substituents (e.g., halogen, alkoxy, amino).

"Aryl" refers to a monovalent, unsaturated aromatic carbocyclic group. Aryl groups include, without limitation, phenyl, naphthyl, anthryl and biphenyl. Aryl groups are unsubstituted or substituted with 1 or more substituents (e.g. halogen, alkoxy, amino). "Arylene" refers to a divalent aryl group.

A "photoacid generator" is a compound or substance which produces acid ($H^+$ or $H_3O^+$) upon exposure to light having a predetermined wavelength.

An "acid scavenger" is a compound or substance which acts to neutralize, adsorb and/or buffer acids, e.g., a base or alkaline compound. Acid scavengers act to reduce the amount or concentration of protons or protonated water, i.e., $H^+$ or $H_3O^+$. In the context of the present invention, an acid scavenger acts to neutralize, diminish, or buffer acid produced by a photoacid generator. Preferably, an acid scavenger exhibits little or no stratification within a film over time or following exposure to heat.

In accordance with an aspect of the present invention, acid scavengers may be further subdivided into "organic bases" and "polymeric bases." A polymeric base is an acid scavenger (e.g., basic unit) attached to a longer polymeric unit. A polymer is typically composed of a number of coupled or linked monomers. The monomers can be the same (to form a homopolymer) or different (to form a copolymer). In a polymeric base, at least some of the monomers act as acid scavengers.

An organic base is defined as a base which is joined to or part of a non-polymeric unit. Non-limiting examples of organic bases include, without limitation, amine compounds (e.g., primary, secondary and tertiary amines). Generally any type of acid scavenger, defined here as a traditional Lewis Base, an electron pair donor, can be used in accordance with the present invention.

In one aspect of the invention, amine compounds are represented by the following structure:

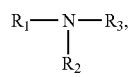

wherein $R_1$, $R_2$ and $R_3$ are independently H, an alkyl group, an alkenyl group, an alkynyl group or an aryl group, or one or more of $R_1$, $R_2$ and $R_3$ taken together with the nitrogen atom form a carbocyclic or heterocyclic ring. In a particular aspect, two or three of $R_1$, $R_2$ and $R_3$ are alkyl groups.

In a particular aspect, one or more of $R_1$, $R_2$ and $R_3$ taken together with the nitrogen atom form a carbocyclic (excluding the pictured nitrogen atom) or heterocyclic ring. For example. $R_1$, and $R_1$, taken together with the nitrogen atom form a ring. In another example, $R_1$ and $R_2$ taken together with the nitrogen atom form a ring and $R_2$ and $R_3$ taken together with the nitrogen atom form a ring. In a further example, $R_1$ and $R_2$ taken together with the nitrogen atom form a ring, $R_2$ and $R_3$ taken together with the nitrogen atom form a ring and $R_1$ and $R_3$ taken together with the nitrogen atom form a ring. Such rings are typically carbocyclic or include only carbon and nitrogen atoms, such as 5-, 6-, 7- and 8-membered rings.

$R_1$, $R_2$ and $R_3$ are often unsubstituted groups, however, substitution is permitted. When $R_1$, $R_2$ and $R_3$ are substituted, substituents can be selected to enhance the solubility of the base.

Exemplary groups of organic base additives include (A) mono, di and tri-alkylamines, (B) anilines and substituted anilines, (C) substituted pyridines, (D) substituted guanidines, (E) bicyclic mono and di-azo compounds, and (F) bifunctional bases containing amino and hydroxyl functionalities. Specific examples of organic base additives are shown below:

| ORGANIC BASE ACID SCAVENGER AND REPORTED BP (MP) | |
|---|---|
| $CH_3-(CH_2)_7-NH_2$ | 175° C. |
| $CH_3-(CH_2)_7-NH-(CH_2)_6-CH_3$ | 297° C. |
| 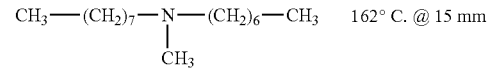 | 162° C. @ 15 mm |
| $CH_3-(CH_2)_7-N-((CH_2)_6-CH_3)_2$ | 365° C. |
| $CH_3(CH_2)_7-N-(CH_3)_2$ | 195° C. |
|  | 88° C. @ 43 mm |
| 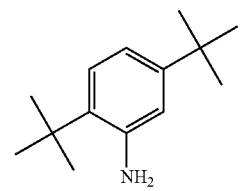 | 104° C. |
| 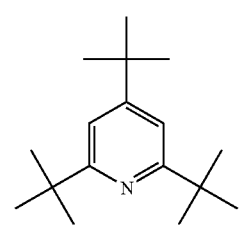 | 115° C. at 20 mm |
| 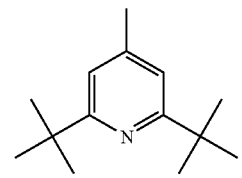 | 233° C. |
| 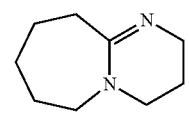 | 115° C. @ 11 mm |
| 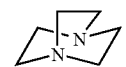 | 159° C. |

| ORGANIC BASE ACID SCAVENGER AND REPORTED BP (MP) | |
|---|---|
|  | 223° C. |
|  | 160° C. |

In accordance with an aspect of the present invention, boiling points and melting points are of great importance in determining whether the compound in question will act as an effective acid scavenger. For example, in some systems a prebake step is employed. If an acid scavenger, particularly an organic base, has a low boiling point, it could tend to evaporate, diminishing the effective amount of scavenger. Thus, if the synthesis methodology employed in the context of the present invention includes exposure of the acid scavenger to a high temperature, a person of skill in the art will compensate by choosing an acid scavenger with a high boiling point or that is a solid at the temperature in question. Alternatively, if a low boiling point acid scavenger is used, a person of skill in the art can compensate for exposure to a high temperature by starting off with a higher concentration of the low boiling point acid scavenger or supplementing the mixture with more acid scavenger to compensate for evaporation.

Organic base concentrations typically range from 0.1 to 4.0 molar equivalents, relative to the PAG. More preferably, organic base concentration rang from 0.1 to 3.0 molar equivalents, such as 0.5 to 2.0 molar equivalents. In accordance with an aspect of the present invention, organic bases advantageously have one or more of the following physical properties: (1) a boiling point above 150° C. and preferably above 200° C., (2) a pKa greater than 7 and less than 14 and more preferably between 8 and 10, (3) a sterically hindered nitrogen, and (4) solubility both in a PAG formulation and in a thin film.

Suitable polymeric bases include basic homopolymers and copolymers, including those formed from amine-containing monomers. Examples of such polymeric bases are polyvinylpyridone, polyvinylpyridine and polyvinylimidizaole. Additional suitable polymeric bases include polymers containing base functionalities (e.g., amines, preferably sterically hindered amines). Further suitable polymeric bases are polymer backbones (e.g., alkylene backbones such as ethylene) to which one or more of the organic bases described above are directly or indirectly attached. In some examples, the nitrogen atom is attached directly or indirectly (e.g., via an alkylene group) to a polymer backbone and $R_3$ is absent. Typically, molecular weights of the polymeric basess range between 2 K and 150 K, more preferably 10 K and 150 K, such as 10 K and 50 K. Polymeric base concentrations generally range from 0.05% to 5% by weight of a film.

A "film" as used herein refers to a layer or coating having one or more constituents, applied in a generally uniform manner over the entire surface of a substrate, for example, by spin coating. For example, in accordance with an aspect of the present invention, a film is a solution, suspension, dispersion, emulsion, or other acceptable form of a chosen polymer. For example, a film can include a photoacid generator and optionally a base and a sensitizer, generally in combination with a film-forming polymer. Film-forming polymers are polymers, which after melting or dissolution in a compatible solvent, can form a uniform film on a substrate.

A "sensitizer" is a compound which aids in the use of certain photoacid generators ("PAGs"). While the instant invention is not limited by any particular mechanism of action or proposed mechanism of action, the sensitizer is understood to extend the photosensitivity of the PAG, i.e., to shift the photo sensitivity to a longer wavelength of electromagnetic radiation. The sensitizer, also called a photosensitizer, is capable of activating the PAG at, for example, a longer wavelength of light in accordance with an aspect of the present invention. Preferably, the concentration of the sensitizer is greater than that of the PAG, such as 1.1 times to 5 times greater, for example, 1.1 times to 3 times greater the concentration of PAG. Exemplary sensitizers suitable for use in the invention include isopropylthioxanthone (ITX) and 10H-phenoxazine (PhX).

A "substrate" is a material having a rigid, semi-rigid or gelatinous surface. Typical examples include glass or suitable polymer materials. In some embodiments of the present invention, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads may be provided on the surface, and compounds synthesized thereon optionally may be released upon completion of the synthesis. Substrates are well known in the art and are readily commercially available through vendors such as USPG, PPG Industries, AFG Industries and others.

A "labile protective group" is a moiety which may be selectively removed to expose an active site such as an amino functionality in peptide or amino acid or a hydroxyl group in a nucleic acid or nucleotide. In accordance with one aspect of the present invention, protective groups may be removed under a variety of condition. For example, an "acid labile protective group" is removed by exposure to acid. For an extensive listing of labile protective groups useful in the practice of the present invention, see also Greene, T. W. and Wuts, P. G. M., Protective Groups in Organic Synthesis, (1991), incorporated herein by reference in its entirety. Useful representative acid sensitive protective groups include dimethoxytrityl (DMT), tert-butylcarbamate (tBoc) and trifluoroacetyl (tFA). Useful representative base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester and the like.

A "predefined region" is a localized area on a substrate which is, was, or is intended to be used for formation of a selected polymer and is otherwise referred to herein in the alternative as "reaction" region, a "selected" region, simply a "region" or a "feature". The predefined region may have any convenient shape, e.g., circular, rectangular, elliptical, wedge-shaped, etc. In accordance with the present invention, the arrays of the present invention have features on the order of 10-100 μm, i.e. 10×10 μm$^2$ to 100×100 μm$^2$ for approximately square features. More preferably the features will be on the order of 1-10 μm. It is also an object of the present invention to provide features having sub-micron dimensions. Such features are preferably on the order of 100-1000 nm. Within these regions, the polymer synthesized therein is preferably synthesized in a substantially pure form. However, in other embodiments of the invention, predefined regions may substantially overlap. In such embodiments, hybridization results may be resolved by software for example.

"Damage to the polymer" means degradation or harm to a polymeric sequence such as deletions or substitutions of one monomer sequence for another, damage to the monomer itself, a linker or substrate. It is an object of the present invention to maintain the integrity of the synthesized polymer in all facets of synthesis and/or use for detection of hybridization or binding. It is an object of one aspect of the present invention that the reagents and conditions used to deprotect the monomer (e.g., exposure of acid labile protective group to acid), whether attached to a linker or growing polymer chain, do not substantially degrade or harm the polymer, monomer, linker or substrate. Preferably, the reagents and conditions used to deprotect will not damage the polymer at all or will do so only minimally such that the polymer can still be specifically recognized by its counterpart (e.g. ligand-receptor). For example, if the polymer is a nucleic acid, it can only sustain damage, e.g., depurination, to the extent that it can still undergo specific Watson-Crick base pairing with a complementary nucleic acid such that specific hybridization is detectable over non-specific hybridizations. Similarly, if a peptide or its amino acids are chemically damaged, the damage must not be to such an extent that a ligand, e.g., an antibody, fails to recognize the peptide. Acceptable levels of damage will be readily appreciated by those of skill in the art. In constructing an array of polymers in accordance with the present invention, it is acceptable that some polymers of a group are extensively damaged as long as there are sufficient other members of the group that are either undamaged or minimally damaged to allow specific recognition of the polymer.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include the corresponding plural references unless the context dictates otherwise. Likewise, plural references include the singular unless the context indicates otherwise.

Throughout this disclosure, various aspects of this invention can be presented in a range format. It should be understood that such description is merely for convenience and brevity and should not be construed as an unwarranted limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques of organic chemistry, polymer technology, molecular biology (including recombinant nucleic acid techniques), cell biology, biochemistry, and immunology as would be understood by one of the ordinary skill. Such conventional techniques include polymer array synthesis, hybridization, ligation, and detection of hybridization using a label. Specific illustrations of suitable techniques can be had by reference to the examples herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer. A Laboratory Manual, and Molecular Cloning. A Laboratory Manual* (all from Cold Spring Harbor Laboratory Press), Stryer, L. (1995) *Biochemistry* (4th Ed.) Freeman, N.Y., Gait, *"Oligonucleotide Synthesis: A Practical Approach"* 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry,* $5^{th}$ Ed., W.H. Freeman Pub., New York, N.Y., all of which are herein incorporated by reference in their entirety.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety.

Patents that describe synthesis techniques in specific embodiments include U.S. Pat. Nos. 5,412,087, 6,147,205, 6,262,216, 6,310,189, 5,889,165, and 5,959,098, which are all incorporated by reference in their entirety. Nucleic acid arrays are described in many of the above patents, but the same general methodologies are applicable to polypeptide arrays.

The present invention also contemplates many uses for polymers attached to substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822, which are all incorporated by reference in their entirety. Genotyping and uses therefore are shown in U.S. Ser. Nos. 60/319,253, 10/013,598 (U.S. Patent Application Publication 20030036069), and U.S. Pat. Nos. 5,856,092, 6,300,063, 5,858,659, 6,284,460, 6,361,947, 6,368,799 and 6,333,179, which are incorporated by reference in their entirety. Other uses are embodied in U.S. Pat. Nos. 5,871,928, 5,902,723, 6,045,996, 5,541,061, and 6,197,506, which are incorporated by reference in their entirety.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entirety. The sample may be amplified on the array. See, for example, U.S. Pat. No. 6,300,070 and U.S. Ser. No. 09/513,300, which are incorporated herein by reference in their entirety.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO 88/10315), self-sustained sequence replication (Guatelli et al., *Proc. Nat. Acad. Sci. USA,* 87, 1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317. Each of the above references is incorporated herein by reference in its entirety.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598, each of which is incorporated herein by reference in its entirety.

Numerous methods for conducting polynucleotide hybridization assays have been well developed. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology,* Vol. 152, Guide to Molecular Cloning Techniques (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which is hereby incorporated by reference in its entirety.

The present invention contemplates detection of hybridization between a ligand and its corresponding receptor by generation of specific signals. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety. Each of these references is incorporated herein by reference in its entirety.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 60/364,731 and in PCT Application PCT/US99/06097 (published as WO 99/47964), each of which also is hereby incorporated by reference in its entirety.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108. Each of these references is incorporated herein by reference in its entirety.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Each of these references is incorporated herein by reference in its entirety.

Light patterns can also be generated using Digital Micromirrors, Light Crystal on Silicon (LCOS), light valve arrays, laser beam patterns and other devices suitable for direct-write photolithography. See, e.g., U.S. Pat. Nos. 6,271,957 and 6,480,324, incorporated herein by reference.

Additionally, the present invention may have preferred embodiments that include methods for providing genetic information over networks such as the Internet as shown in U.S. Ser. No. 10/063,559 (United States Publication No. 20020183936) and U.S. Provisional Applications 60/349, 546, 60/376,003, 60/394,574 and 60/403,381). Each of these references is incorporated herein by reference in its entirety.

The present invention provides methods, devices, and compositions for the formation of arrays of large numbers of different polymer sequences. In one aspect of the present invention, the methods and compositions provided herein involve the conversion of radiation signals into chemical products that are particularly useful in polymer synthesis. The invention also includes the arrays formed using the methods and compositions disclosed herein. One aspect of the invention includes methods, compositions, and devices for the synthesis of an array of different polymers in selected and predefined regions of a substrate. Another aspect of the invention includes those arrays and various methods of using them.

Such arrays are used in, for example, in nucleic acid analysis. Polynucleotide or nucleic acid arrays are especially suitable for checking the accuracy of previously elucidated sequences and for detecting mutations and polymorphisms. Polymer arrays are also used in screening studies to evaluate their interaction with, for example, receptors such as antibodies in the case of peptide arrays or with nucleic acids in the case, for example of oligonucleotide arrays. For example, certain embodiments of the invention provide for the screening of peptides to determine which if any of a diverse set of peptides has strong binding affinity with a receptor.

In some embodiments of the present invention, the arrays formed by the present invention are used in competitive assays or other well-known techniques to screen for compounds having certain activities. For example, vast collections of synthetic or natural compounds are immobilized on predefined regions of a substrate. The reaction of the immobilized compounds (or compound) with various test compositions such as the members of a chemical library or a biological extract are tested by dispensing small aliquots of each member of the library or extract to a different region. In one embodiment, a large collection of human receptors is deposited on a substrate, one in each region to form an array. A plant or animal extract is then screened for binding to various receptors of the array.

Nucleic acid sequences can also be immobilized in specific locations or predefined regions of a substrate using the current invention. In some embodiments, such immobilized nucleic acid arrays are used in hybridization assays for gene expression monitoring, nucleic acid amplifications, nucleic acid computation, and nucleic acid analysis in general.

The present invention has certain features in common with the radiation directed methods discussed in U.S. Pat. No. 5,143,854, incorporated herein by reference. The radiation-directed methods discussed in that patent involve activating predefined regions of the substrate and then contacting the substrate with a preselected monomer solution. The predefined regions can be activated with, for example, a light source shown through a mask (much in the manner of photolithographic techniques used in integrated circuit fabrication). Other regions of the substrate remain inactive because they are blocked by the mask from illumination. Thus, a light pattern defines which regions of the substrate react with a given monomer. By repeatedly activating different sets of predefined regions and providing different monomer compositions thereto, a diverse array of polymers is produced on or near the substrate.

According to another aspect of the present invention, there is no requirement for the use of masks. Predefined regions of the array may be activated by light without the use of photomasks, for example without limitation, by spatial light modulation as discussed in U.S. Pat. No. 6,271,957 and related applications (parent and progeny patents).

According to one aspect of the present invention, linker molecules having reactive functional groups protected by acid labile protecting groups are provided on the surface of a substrate. In one preferred embodiment of the present invention, a photoacid generator ("PAG") is provided on the surface, preferably in a film with an acid scavenger. This is also called a "resist mixture."

In another aspect of the present invention, the resist mixture additionally contains a sensitizer. A set of selected regions on the surface of the substrate is exposed to radiation using well-known lithographic methods discussed, for example, in Thompson, L. F.; Willson, C. G.; and Bowden, M. J., Introduction to Microlithography; *American Chemical Society*, 1994, pp. 212-232, incorporated herein by reference in its entirety.

According to an aspect of the present invention, acid is generated in the selected regions from the PAG by exposure of the PAG to light of a predetermined wavelength. The generated acid contacts the protected group(s) for long enough and under appropriate conditions to remove the protective group. In accordance with an aspect of the present invention, the protective group is preferably a DMT group and it protects a hydroxyl group. The hydroxyl group can be, for example, part of a substrate, part of a linker, a 5'-hydroxyl group of a nucleotide or deoxynucleotide or a 3'-hydroxyl group of a nucleotide or deoxynucleotide. After sufficient exposure of the protective groups to the acid such that the protective group is removed, but no or substantially no damage is done to any polymer, the surface of the array is stripped, preferably in an appropriate solvent leaving protected and unprotected groups. In one aspect of the invention, the protective groups are exposed to the acid for up to 3 hours, such as up to 1 hour, and typically from 2-30 or 5-15 minutes.

Monomers having an acid labile protective group are allowed to react with the exposed groups from the acid treatment. The surface is again coated with one of the resist mixtures described above.

In a particular embodiment of the invention, deoxynucleotides having one hydroxyl group with an acid labile protective group and the other with a reactive group, preferably a phosphoramidite group, are allowed to react with the exposed hydroxyl groups from the acid treatment, allowing coupling of the nucleotide to the hydroxyl group. The surface is again coated with one of the resist mixtures described above.

A second set of selected regions is, thereafter, exposed to radiation. The radiation-initiated reactions remove the protecting groups on molecules in the second set of selected regions, i.e. the linker molecules and the first-bound monomers. The substrate is then contacted with a second monomer containing a removable protective group for reaction with exposed functional groups. This process is repeated to selectively apply monomers until polymers of a desired length and desired chemical sequence are obtained. According to one aspect of the present invention, the monomers are preferably nucleotides. In accordance with an aspect of the present invention, growing chains of nucleic acid are preferably capped in between synthesis rounds. By terminating chain growth where a monomer should have been added but was not, capping limits the production of incorrect nucleotide sequences. Side chain protective groups for exocyclic amines for example are also preferably protected by techniques well known in the art during synthesis and deprotected at the conclusion of synthesis of the nucleotide array.

In one preferred embodiment, the monomer is a 2'-deoxynucleoside phosphoramidite containing an acid labile protecting group at its 5'-hydroxyl group. Accordingly, a "monomer" is understood to include both the individual units of a finished polymer (e.g., oligonucleotide, polypeptide) and compounds that become individual units of a finished polymer upon attaching to a substrate and optionally further reaction (e.g., to remove protecting groups, to oxidize phosphite esters to phosphate esters). As stated previously, in an alternate embodiment, the protecting group is present at the 3'-hydroxyl group if synthesis of the polynucleotide is from the 5' to 3' direction. The nucleoside phosphoroamidite is represented in accordance with one aspect of the present invention by the following formula:

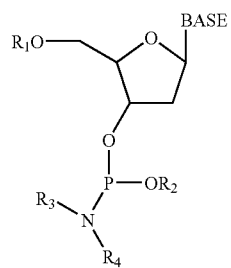

wherein the base is adenine, guanine, thymine, or cytosine, $R_1$ is a protecting group which makes the 5' hydroxyl group unavailable for reaction and includes dimethoxytrityl, tert-butyloxycarbonyl or any of the protecting groups known to those of skill in the art; $R_2$ is cyanoethyl, methyl, t-butyl, trimethylsilyl or the like; and $R_3$ and $R_4$ are isopropyl, cyclohexyl and the like. Exocyclic amines present on the bases can also be protected with acyl protecting groups such as benzoyl, isobutyryl, phenoxyacetyl and the like. The linker molecule contains an acid- or base-removable protecting group. Useful linker molecules are well known to those skilled in the art and representative examples include oligo ethers such as hexaethylene glycol, oligomers of nucleotides, esters, carbonates, amides and the like. Useful protecting groups include those previously listed and others known to those skilled in the art.

In another preferred embodiment, the monomer is an amino acid containing an acid- or base-removable protecting group at its amino or carboxy terminus and the linker molecule terminates in an amino or carboxy acid group bearing an acid- or base removable protecting group. Protecting groups include tert-butyloxycarbonyl, 9-fluorophenylmethoxycarbonyl, and any of the protective groups previously mentioned and others known to those skilled in the art.

According to one aspect of the present invention, spatially defined polymer synthesis will be performed by depositing a photoresist such as Ghand's "VLSI Fabrication Principles," Wiley (1983), incorporated herein by reference in its entirety. According to these embodiments, a resist is deposited, selectively exposed, leaving a portion of the substrate exposed for coupling. These steps of depositing resist, selectively removing resist and monomer coupling are repeated to form polymers of defined sequences at desired locations. In some specific embodiments, a positive tone resist comprised of diazonapthoquinone-novolac (DQN/N) is incorporated in a creasole-formaldehyde polymer matrix. This resist and its variants are used routinely in the microelectronics industry for submicron resolution lithography, as more fully discussed in Reiser, "Photoreactive Polymers: The Science and Technology of Resist," Riley (1989), incorporated herein by reference in its entirety. However, it has been discovered in accordance with an aspect of the present invention that substantial and non-obvious refinements to the procedures developed for the microelectronics industry are necessary to allow similar procedures to work with certain polymers of the present invention, e.g., nucleic acids. It is also known to those of skill in the art that other polymers such as peptides are not stable at all conditions employed in the microelectronics industry.

High contrast detritylation of less than 4 microns has been demonstrated with simple contact printing with a resist. Unfortunately, the alkaline conditions needed (aqueous [OH] of 0.1 M) complicates its direct use in a multistep polymer synthesis, such as polynucleotide array fabrication because of the hydrolysis of nucleobase exocyclic amine protecting groups that are used to prevent side reactions during synthesis with standard phosphoramidite monomers.

As various well known methods for chemical removal of protecting groups involving application of alkali conditions resulted in undesired side reactions such as removal of exocyclic amino protecting groups, reagents and methods were developed for light-directed synthesis of DNA probes, utilizing phosphoramidite monomers having photolabile protecting groups. These methods and reagents are described in the various references incorporated by reference above.

Under some circumstances, photodeprotection yields truncated probe sequences due to incomplete removal of the photoprotecting group following application of light. Incomplete removal of a photodeprotecting group may impose limitations on probe length. For example, if one imagines a stepwise yield of photolysis of 85% and 25 successive steps are carried out to provide 25-mer oligonucleotides, less than 2% of the probes will reach the desired length of 25.

In addition, relative to conventional DMT-protected phosphoramidite monomers, photolabile-protected phosphoramidite monomers are costly to obtain. A manufacturing process that uses DMT-protected phosphoramidite monomers should therefore be cheaper, and by analogy to well-established efficiencies of acid-mediated DMT removal, should also be higher-yielding, perhaps even approaching a 99% stepwise yield. A high-yielding synthesis method would substantially decrease the number of truncated probes and enable the ability to produce long-mer probes (e.g., 50-mer, 60-mer, 70-mer etc.) with relative ease. Shorter probes could also be constructed by the same method if desired.

In accordance with one aspect of the present invention, methods and compositions to generate localized photo-generation of appropriate acid species to effect protecting group (e.g., DMT) removal from growing strands of polynucleotides were developed. The traditional semiconductor field employs photoacid generator compounds (i.e., PAGs) in conjunction with "sensitizer" compounds.

Sensitizer compounds work to allow some PAGs to produce acid at an acceptable wavelength of light. Many PAGs are known from the computer chip industry. Many of them require activation energies, i.e., wavelengths of light, which can cause damage to the DNA being synthesized on the substrate. For example wave lengths of light which are perfectly tolerable for computer chips (<300 nm) would cause severe damage to DNA oligonucleotides, rendering these PAGs useless for oligonucleotide array synthesis. However, an appropriate sensitizer can render the same PAG activatable by longer wavelengths of light.

In the computer chip industry, after exposure of PAGs to light a baking step is traditionally employed to maximize the effect of the liberated acid. However, a traditional baking step is likely to lead to substantial damage in the way of depurination of the probes. Probes which have undergone depurination, i.e., the loss of the base structure on A and G nucleotides, will not hybridize as well, or possibly at all, to corresponding homologous DNA or RNA.

Solutions to acid induced depurination are known in the art. Analogues of standard DNA, for example 2'-O-methyl (2'-OMe) nucleoside modifications, are known to be more resistant to such degradation. However, utilization of such analogues is substantially more expensive than the corresponding underivatized analog. Moreover, analogues such as 2'-OMe nucleosides alter the hybridization properties of the probes, which would require changes to probe/array design.

In accordance with the present invention, probes may be prepared using standard DMT-containing monomers and detritylation with a photoacid generator used under appropriate conditions, i.e., conditions described in accordance with an aspect of the present invention that substantially reduce or eliminate acid induced depurination. In accordance with an aspect of the present invention, the exposure time of the polymer to the acid is an important consideration. Another key aspect of an aspect of the invention is the photolysis time, which must be of sufficient duration to generate a suitable quantity of acid and achieve essentially quantitative detritylation, but not so long that depurination becomes a factor. It has been discovered in accordance with an aspect of the present invention that a heating step following photoactivation of the PAG, which is routinely employed and taught in the semiconductor industry, should not be used in conjunction with certain polymers contemplated by the present invention, including especially polynucleotides, e.g. DNA oligonucleotides. If growing polynucleotide chains are baked after activation of the photoacid generator, it appears that the resulting heat in conjunction with a localized low pH causes depurination. Thus, post-UV light exposure baking is to be avoided in accordance with an aspect of the present invention.

In accordance with this aspect of the present invention, the photoacid causes minimal or insubstantial damage to the polymers making up the array. What damage may be endured by the polymer in question will be determined by the nature of the polymer and the assay or experiment to be conducted with the array. This will be apparent to the person of skill in the art. For example, if an array of oligonucleotides is fabricated, a certain amount of depurination may be tolerated if the probes on the array can still be used to reliably and specifically detect sequences in a sample. Preferably, depurination occurs in less than 25%, less than 20%, less than 15%, less than 10%, less than 5%, less than 3%, less than 2% or less than 1% of nucleotides susceptible to depurination.

In accordance with another aspect of the present invention, the PAG must be chosen (in conjunction with a sensitizer as necessary) such that that wavelength of light of activation does not fall below about 310 nm. For example, many PAGs used in the semiconductor industry require UV light having a wavelength of less than 300 nm. Indeed, literature references speak of using "short UV" PAGs wherein wavelengths of light of 220 to 260 nm are used. In accordance with an aspect of the present invention, such short UV wavelengths are unacceptable with respect to nucleic acids. For nucleic acids, UV light of wavelength greater than 310 nm, such as 330 to 365 nm is typically used. More preferably, UV light of around 365 nm is used.

According to one aspect of the present invention a process is provided for fabricating an array of polymers, the process having the steps of providing a substrate having a reactive group protected by a protective group; coating the substrate with a film having an activatable deprotecting agent; activating the deprotecting agent in selected regions by selective application of an activator to provide an activated deprotecting agent; and exposing the monomer having the protective group to the activated deprotecting group under appropriate conditions such that the protecting group is removed to provide an exposed reactive group wherein the step of exposing does not result in substantial damage to the polymer. In accordance with the present invention, the reactive group may be located on a linker having one end bound to a substrate with the reactive group at the opposite end or other exposed site of the linker, a monomer attached to a linker or a polymer (here, two or more monomers) attached to a linker.

Typically, the array of polymers is an array of nucleic acids. More typically, the array of nucleic acids is an array of oligonucleotides. The monomers for such arrays are preferably naturally or non-naturally occurring nucleotides. More preferably, the nucleotides employed in the present invention are selected from the group consisting of G, A, T, and C. Preferably, a nucleotide is protected at its 5' hydroxyl end by a dimethoxytrityl ("DMT") protective group. In the most preferred embodiments, the nucleotide is selected from the group G, A, T, and C and is protected at its 5' hydroxyl group by a DMT protective group. In another aspect of the present invention, the nucleotide is protected at its 3' hydroxyl group with a DMT protective group. Thus, in accordance with the present invention, nucleotides may be synthesized in the 5' to 3' direction or a 3' to 5' direction.

In still another preferred embodiment of the present invention, the array of polymers is an array of peptides, where the monomers are amino acids. Suitable amino acids include naturally occurring amino acid and non-naturally occurring amino acids. Preferably, the amino acid is selected from the group consisting of the L form of alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine and valine. Preferably, an amino acid is protected at its amino terminus functionality by a tert-butyloxycarbonyl ("tBOC") protective group during synthesis.

According to another aspect of the present invention, suitable amino acids include peptide nucleic acids (PNAs). PNAs include a peptide backbone with nitrogenous bases attached to this backbone, such that they can serve as mimics of nucleic acids (including oligomers). Preferably, PNAs have a greater affinity for a complementary nucleic acid sequence than the analogous native nucleic acid. Suitable PNA repeat units are shown by the following structural formulae:

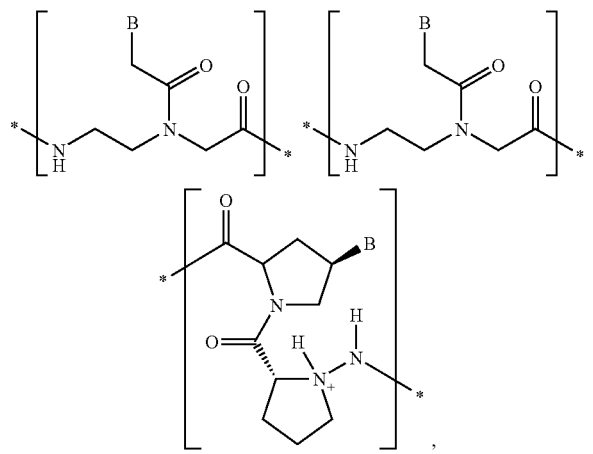

where B represents a base-typically adenine, cytosine; guanine or thymine. Other backbones are suitable, provided that the resulting PNAs are capable of hybridizing with nucleic acids.

Syntheses of PNAs are described in Hyrup and Nielsen, *Bioorg. Med. Chem.* (1996) 4:5-23; and Vilaivan and Lowe, *J. Am. Chem. Soc.* (2002) 124:9326-9327, the contents of which are incorporated herein by reference.

In an aspect of the invention, density of PNAs in an array and any linker groups are selected such that a 2:1 complex of PNA to a hybridized DNA or RNA sample can be formed. In another aspect of the invention, a chimeric polymer of PNA and a nucleic acid is prepared.

In another aspect of the instant invention, the process described above has an additional step of reacting the monomer with an exposed reactive group with a second monomer having a reactive group protected by a protective group. In another preferred embodiment of the instant invention, the process further includes repeating all the steps to obtain the desired polymer array.

Originally the term lithography referred to a method of printing using a nonpolar ink applied to a hydrophilic master plate patterned with a hydrophobic image. As used at the present date, the term is generally used to describe a number of methods for replicating a predetermined master pattern on a substrate. Common applications of this technology involve replication effected by first coating the substrate with a radiation-sensitive polymer film (a resist) and then exposing the film to actinic radiation in a predefined pattern. The radiation-induced chemical changes that result, alter the chemical properties of the exposed regions of the coated substrate such that they can be differentiated in subsequent developmental steps.

In yet another preferred embodiment of the instant invention, the step of coating is performed by applying to the substrate a film of a polymer solution containing the activatable deprotecting agent. Preferably, the polymer solution is a composition of a certain percentage of poly(methyl methacrylate). Preferably, the activatable deprotecting agent is a photoacid generator.

One group of photoacid generators of the invention is represented by Structural Formula (I):

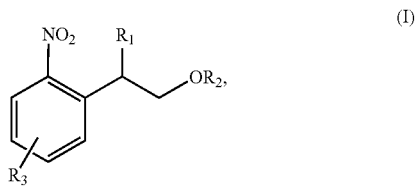

or a salt thereof, wherein:

$R_1$ is —H, —COOR, a substituted alkyl group, or an alkenyl or aryl group;

$R_2$ is a sulfonate, substituted acetate or benzoate group;

$R_3$ is —NRR', —COOR, an alkyl or alkenyl group or a substituted alkoxy or aryl group; and R and R' are independently —H or an alkyl, alkenyl or aryl group.

A second group of photoacid generators of the invention is represented by Structural Formula (II):

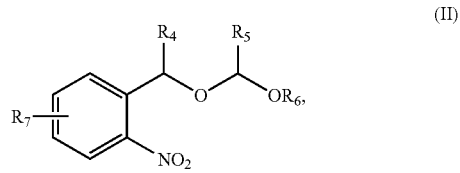

or a salt thereof, wherein:

$R_4$ and $R_5$ are independently —H, —COOR, a substituted alkyl group or an alkenyl or aryl group;

$R_6$ is a sulfonate, substituted acetate or benzoate group;

$R_7$ is —NRR', —COOR, an alkyl or alkenyl group or a substituted alkoxy or aryl group; and R and R' are independently —H or an alkyl, alkenyl or aryl group.

A third group of photoacid generators of the invention is represented by Structural Formula (III):

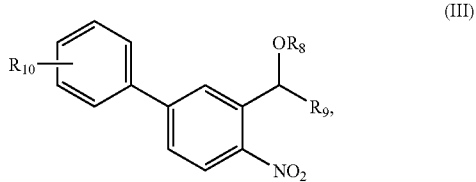

or a salt thereof, wherein:

$R_8$ is a sulfonate, substituted acetate or benzoate group;

$R_9$ is —H, —COOR, a substituted alkyl group or an alkenyl or aryl group;

$R_{10}$ is —NRR', —COOR, an alkyl or alkenyl group or a substituted alkoxy or aryl group; and R and R' are independently —H or an alkyl, alkenyl or aryl group.

Where the activatable deprotecting agent is a photoacid generator, it is particularly preferred that the monomer is a nucleotide and the protecting group is DMT. It is also preferred in this situation that the monomer is an amino acid and the protecting group is tBOC.

In other embodiments of the instant invention, the array of polymers comprises a polymer at least 25 monomers in length. In another preferred embodiment, the polymer is at least 50 monomers in length. In further embodiments, the polymer may range up to 200 monomers in length. In other preferred embodiments, the polymers are at least 60, 70, 80, 90, 100, 110, 120, 130, 140 or 150 monomers in length. More preferably, the polymers referred to above are nucleic acids or oligonucleotides.

Still other photoacid generators ("PAGs") are known and suitable for use in the present invention, such as combination with the PAGs represented by Structural Formulae (I)-(III) or separately in certain steps of a synthetic process. Common commercial ionic PAGs include onium and organometallic salts such as diaryliodonium and triarylsulfonium salts and (cyclopentadienyl)(arene)iron$^+$ salts of the anions $PF_6^-$, $SbF_6^-$, $CF_3SO_3^-$, $C_4F_9SO_3^-$ and $C_8F_{17}SO_3^-$. Also known are sulfonium salts (e.g., triphenylsulfonium hexafluorophosphate, triflate, toslyate, and camphorsulfonate). PAGs previously used in the synthesis of biological polymers include 2,6-dinitrobenzyl tosylate and Bis (4-t-butyl phenyl) iodonium $PF_6^-$.

The photochemical reaction of many onium salts generates a strong Brönsted acid. In this regard, numerous PAGs are known from the semiconductor industry. However, in the semi-conductor industry, the wafer is subjected to a baking step after generation of the acid by photolysis, where the exposed wafers are subjected to elevated temperatures. In accordance with the present invention, it has been discovered that baking has a deleterious effect on some polymers, in particular nucleic acids. Thus, while onium salts and other PAGs used in the semiconductor industry are of interest to the present invention, protocols for the usage of these compounds must be varied significantly as described in accordance with one aspect of the present invention.

Onium salts are known to have high quantum yields of acid production, good absorption properties and good solubility in many resist films. However, it is also known in accordance with the present invention that the wavelengths of light commonly used to activate onium salts for semi-conductors can not be used with some polymers, particularly nucleic acids. In this regard, it is common in the semi-conductor industry to use low wavelength UV light (e.g. less than 300 nm) to activate onium salts. See, e.g., Wallraff, G. M. and Hinsberg, W. D., *Lithographic Imaging Techniques for the formation of Nanoscopic Features*, Chem. Rev. 1999, 99, 1801-1821, which is incorporated herein be reference for all purposes.

In accordance with the present invention, it is known that such wavelengths of light are unacceptable for the synthesis of nucleic acids. Such wavelengths of UV light cause numerous forms of damage to a nucleic acid chain, including cross-linking of bases. Nucleic acids synthesized under these conditions would be unable to effectively hybridize to their homologous counterparts. To use PAGs in accordance with the present invention, they must be capable of being directly or indirectly activated by light in the range of 330 nm to about 365 nm and generate acid at an acceptable level and rate (photospeed) at those longer wavelengths.

In accordance with an aspect of the present invention, both ionic and non-ionic photoacid generators are contemplated to be used in combination with the photoacid generators represented by Structural Formulae (I)-(III). Ionic PAGs are thermally stable and have a wide range of spectral absorption. However, ionic PAGs have a limited solubility in organic solvents. Non-ionic PAGs have better solubility in organic solvents, but have less thermal stability than ionic PAGs. However, as discussed above, the thermal stability is a less important consideration here than in the computer industry.

In accordance with an aspect of the present invention, the polymers synthesized by the techniques of the present invention do not undergo undue or substantial damage during the synthesis. In this regard, it is known that exposure of nucleic acid polymers to acids can result in damage, including for example depurination. In the context of nucleic acid arrays, which are used to detect the hybridization of homologous species of nucleotides, the nucleic acid attached to the substrate can undergo some depurination and still act to satisfactorily hybridize homologous nucleic acids. However, if the damage is too great, the hybridization will not occur at all or will not occur reliably. A substantial number of damaged probes in a feature could result in a false negative. Thus, in certain embodiments of the instant invention, the acid from a photoacid generator is not allowed to substantially damage the nucleic acids being synthesized. In accordance with the present invention, substantial damage means that the polymer or nucleic acid is unable to be used for the intended use for the array. Thus, in the context of a nucleic acid array, substantial damage would mean that the array could not be used to reliably detect nucleic acids. For a protein array, substantial damage would mean that the peptide was damaged to the extent that it could not be recognized by an antibody or protein receptor.

In one aspect of the present invention, the polymer is a nucleic acid and the monomer is a nucleotide and substantial damage is determined by determining the level of false negatives (e.g., the loss of signal from hybridization) generated by hybridizing the array with a known sample having known complementary nucleic acids to said array. In accordance with this aspect, the array can be tested by hybridizing it with a test or control sample having nucleic acids which should give a positive signal on the array if the oligonucleotides, for example, on the array have been synthesized without substantial damage. After hybridization of the control sequence, the array can be scanned and the features analyzed with the corresponding control probes. If the control probes have suffered no damage during fabrication, a high intensity result should be observed. However, if minimal damage occurred the signal might still be present, but diminished, for example by 50%. If the array were intended to detect rare species such a diminution would probably be unacceptable. The batch of arrays containing such defects would likely be disposed of. If no signal were seen or if the signal was diminished by 90% or more, the batch of such arrays would probably be disposed of regardless of the proposed end use of such arrays.

In accordance with another aspect of the present invention, the polymer arrays generated by the teachings of instant invention are subjected to quality control. In preferred embodiments, oligonucleotide or nucleic acid arrays of the present invention are subject to quality control to determine fidelity of the synthesis and the ability of the probes to bind to homologous nucleic acids. In a preferred embodiment of the present invention, quality control is performed by synthesizing nucleic acid arrays containing probes of known sequence. These arrays are then hybridized to control sequences corresponding to the known sequence. It is then determined whether sufficient signal is generated by hybridization to the control sequences.

In preferred embodiments, the arrays are synthesized on wafers, containing scores of joined individual arrays. Quality control is performed on a wafer by sawing off a few arrays for the control testing described above. According to an aspect of the instant invention, if the few arrays pass the control hybridization test, the wafer passes the test and it then may be segregated into individual arrays. If the control experiments fail, the wafer fails and is discarded.

In accordance with another aspect of the present invention, an array of oligonucleotides is produced using a PAG and DMT protected nucleotides to produce features preferably on the order of 10-100 μm. More preferably, features are on the order of 1-10 μm. In another preferred embodiment, features are on the order of 100-1000 nm.

In accordance with an aspect of the present invention, one purpose of adding an acid scavenger to the resist mixture is to modulate contrast/sensitivity and decrease background (e.g., spontaneous detritylation).

In accordance with an aspect of the present invention, standard DMT-protected phosphoramidite nucleotide monomers are used in conjunction with one or more acid scavengers. Generally, an activated DMT-protected phosphoramidite monomer is coupled to a support-bound hydroxyl functionality and oxidized in the typical manner. The support (i.e., wafer or chip) is subsequently coated with a PAG formulation that contains a photoacid generator, a polymeric matrix, solvent and an acid scavenger. Preferably, an acid scavenger is either an organic base or a polymeric base described herein.

In a preferred embodiment of the present invention, arrays of the instant invention are synthesized on commercially available silicon wafers.

The foregoing invention has been described in some detail by way of illustration and examples, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound represented by Structural Formula (III):

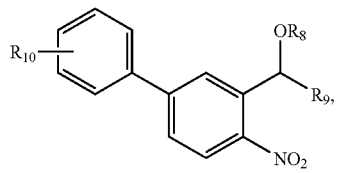

(III)

or a salt thereof, wherein:
$R_8$ is a substituted sulfonyl, acetyl or benzoyl group;
$R_9$ is —H, —COOR, a substituted alkyl group or an alkenyl or aryl group;
$R_{10}$ is —NRR', —COOR, an alkyl or alkenyl group or a substituted alkoxy or aryl group; and
R and R' are independently —H or an alkyl, alkenyl or aryl group.

2. A method of generating acid, comprising exposing to light of an appropriate wavelength a compound represented by Structural Formula (III):

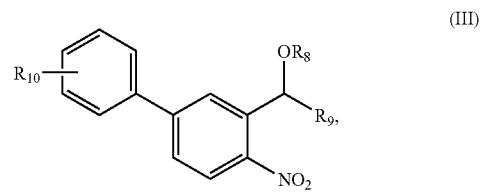

(III)

or a salt thereof, wherein:
$R_8$ is a substituted sulfonyl, acetyl or benzoyl group;
$R_9$ is —H, —COOR, a substituted alkyl group or an alkenyl or aryl group;
$R_{10}$ is —NRR', —COOR, an alkyl or alkenyl group or a substituted alkoxy or aryl group; and
R and R' are independently —H or an alkyl, alkenyl or aryl group.

3. The method of claim 2, wherein the compound is exposed to light in the presence of a sensitizer.

4. A process for fabricating an array of polymers comprising: (a) providing a solid substrate comprising a reactive group protected by an acid labile protective group; (b) coating said solid substrate with a film, said film comprising a photoacid generator represented by Structural Formula (III):

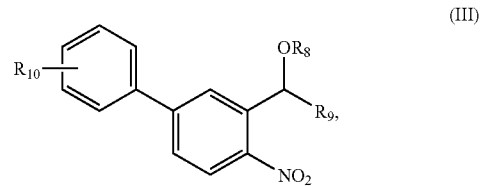

(III)

or a salt thereof, wherein:
$R_8$ is a substituted sulfonyl, acetyl or benzoyl group;
$R_9$ is —H, —COOR, a substituted alkyl group or an alkenyl or aryl group;
$R_{10}$ is —NRR', —COOR, an alkyl or alkenyl group or a substituted alkoxy or aryl group; and
R and R' are independently —H or an alkyl, alkenyl or aryl group;
(c) activating said photoacid generator in selected regions of said substrate by selective application of light having a predetermined wavelength to provide an acid;
(d) exposing said reactive group having said protective group to said acid such that said protective group is removed to provide an exposed reactive group;
(e) reacting said exposed reactive group with a monomer, wherein the monomer is coupled to said exposed reactive group; and
(f) repeating the steps of coating, activating, exposing and reacting to produce the array of polymers.

5. A process according to claim 4, wherein said film further comprises an acid scavenger.

6. A process according to claim 4, wherein said polymer is a nucleic acid.

7. A process according to claim 4, wherein said polymer is a polypeptide.

* * * * *